(12) United States Patent
Ebstein

(10) Patent No.: US 7,515,681 B2
(45) Date of Patent: Apr. 7, 2009

(54) HIGH RESOLUTION PROTON BEAM MONITOR

(75) Inventor: Steven M. Ebstein, Newton, MA (US)

(73) Assignee: Lexitek, Inc., Wellesley, MA (US)

( * ) Notice: Subject to any disclaimer, the term of this patent is extended or adjusted under 35 U.S.C. 154(b) by 0 days.

(21) Appl. No.: 11/629,380

(22) PCT Filed: Jun. 30, 2005

(86) PCT No.: PCT/US2005/023747

§ 371 (c)(1),
(2), (4) Date: Dec. 12, 2006

(87) PCT Pub. No.: WO2006/005059

PCT Pub. Date: Jan. 12, 2006

(65) Prior Publication Data

US 2007/0181815 A1    Aug. 9, 2007

Related U.S. Application Data

(60) Provisional application No. 60/584,050, filed on Jun. 30, 2004.

(51) Int. Cl.
*A61B 6/00*    (2006.01)
(52) U.S. Cl. ....................................................... 378/19
(58) Field of Classification Search .................... 378/19
See application file for complete search history.

(56) References Cited

U.S. PATENT DOCUMENTS

| 3,980,885 | A | * | 9/1976 | Steward et al. | 250/307 |
| 4,058,832 | A | * | 11/1977 | Vagi | 348/162 |
| 5,233,990 | A | * | 8/1993 | Barnea | 600/427 |
| 5,704,890 | A | * | 1/1998 | Bliss et al. | 600/1 |

OTHER PUBLICATIONS

Schultz L J et al., "A narrow-gap ion chamber for beam motion correction in proton radiography experiments" Aug. 11, 2003. Nuclear Instruments & Methods In Physics Research, pp. 220-226.
Kwiatkowski K et al., "Development of multi-frame detector for ultra-fast radiography with 800 MeV protons" Oct. 15, 2000, Nuclear Science Symposium Conference Record, pp. 6-129.

* cited by examiner

*Primary Examiner*—David P Porta
*Assistant Examiner*—Kiho Kim
(74) *Attorney, Agent, or Firm*—Bromberg & Sunstein LLP

(57) ABSTRACT

A method and apparatus for monitoring a scanning beam of penetrating radiation, such as a scanning proton beam used to irradiate tissue. The position of the beam is tracked in real time by interposing a scintillator film between a source and an object of irradiation. An imaging detector, in optical communication with the scintillator, provides an output that is indicative of the position of the radiation and its variation with time. The accumulated dose over a scan may also be monitored.

18 Claims, 3 Drawing Sheets

HIGH RESOLUTION PROTON BEAM MONITOR

FIELD OF THE INVENTION

The present invention pertains to a device and a method for monitoring, in real time, the spatial characteristics of a beam of penetrating radiation, and, more particularly, to a screen incorporating scintillator material that is disposed within the beam and that is optically imaged while a target object is irradiated.

BACKGROUND ART

Proton Therapy

An objective of radiation therapy is to maximize and conform absorbed dose to a specified target volume that has been determined to contain diseased tissue, while, at the same time, minimizing dose to surrounding healthy tissue. The conformation of dose typically requires the use of multiple beams and control, dynamic or static, of the available geometric and dosimetric beam parameters. A unique advantage of charged particle beams, including protons or heavier ions, is the ability to control the penetration depth of the radiation dose, i.e., the Bragg peak location. This results in significant dosimetric advantages of even static proton beams compared to other forms of radiation delivery. The improved dose localization permits higher tumor doses with increased sparing of normal tissue doses. Thus, both an increase in tumor control and a reduction in radiation morbidity are expected. The relative energy deposition along the direction of the beam of single proton and photon beams is compared in FIG. 1. The upper curve 10 represents the dose delivered by a photon beam as a function of depth into the subject tissue. Upper boundary 12 of the filled region of the figure denotes a 'pristine proton Bragg peak,' the dose delivered by a mono-energetic beam of protons. The 'spread out Bragg peak' (SOBP) 14 arises due to a spread in photon energies. The blank region 16 between the curves 10 and 14 corresponds to excess dose delivered by a photon beam relative to a charged-particle beam.

Over 20 hospital-based facilities world-wide now treat patients with proton beams, and more are under development.

Conformality in proton dose distribution is improved through the use of Intensity Modulated Proton Radiotherapy (IMPT). This technique uses a dynamically intensity and position controlled narrow-focused "pencil" beam of protons to precisely control the dose at individual points in the target volume inside the patient. The beams have intensity distributions with full-width half-maximum (FWHM) dimensions typically between 5.0 to 10.0 mm. Some IMPT beam delivery uses a raster scanning technique, effectively painting layer by layer, modifying the range of the protons in between layers. Another form of IMPT is the spot scanning approach which deposits dose at all the required ranges at a given spot and then the beam is moved to the next spot. A typical magnetic scanning speed is about 20,000 mm/sec. This implies beam motion of 5 mm in 250 μsec.

In a typical scenario for IMPT, a treatment fraction is administered by delivering multiple beams. Each beam has a series of 10 or so different layers, each of which has a different proton energy or penetration depth. Each layer has a corresponding 2-D intensity or fluence profile. With a dose on the order of a centigray per layer, each layer will take on the order of 30 seconds to deliver and treatment fractions may last on the order of 5 minutes. The 30 second time frame is the period over which the spatial distribution of proton intensity must be controlled. During this period, the same nominal intensity pattern will be scanned across the patient multiple times, at least several times per second. The number and frequency of scans is such that each scan has a small enough dose that any errors in the scan can be corrected by subsequent scans.

Solid, inorganic scintillators have been used, in conjunction with radiation therapy, for absorbed dose measurement (as described, for example, by J. M. Schippers, S. N. Boon and P. van Luijk, "Applications in Radiation therapy of a scintillating screen viewed by a CCD camera," Nucl Instr. and Meth. A 477, pp. 480-85 (2002), and S. N. Boon, thesis, "Dosimetry and quality control of scanning proton beams" (1998), and references therein, all of which are incorporated herein by reference. Similarly, solid scintillators have been applied in therapeutic beam profiling and computer tomography. In all these cases, the scintillator must either be positioned in the beam in place of the tissue to be irradiated, or disposed to receive the irradiating beam after it has traversed the tissue.

A gas scintillator has been described by G. Coutrakon et al. ("A beam intensity monitor for the Loma Linda cancer therapy proton accelerator," *Medical Phys.*, vol. 18(4), pp. 817-20 (1991)) for application to proton irradiation therapy, for monitoring overall beam intensity, and proving a real time feedback for beam intensity stabilization, however, the use of a gas scintillator imposes containment and other difficulties.

Requirements for Real-Time Tracing Detectors

Scanning proton or ion beams are used in conjunction with real-time imaging or tracking detector for monitoring the beam. Monitoring detectors currently employed in scanning proton therapy systems are briefly surveyed. As with doubly scattered proton therapy, there are several direct and indirect monitors of the beam fluence and energy, including at least one ionization chamber close to the exit port of the nozzle through which the protons are channeled to the irradiated tissue. Scanning systems also have monitors for the current in the deflection magnets in the nozzle.

It has been proposed to use indirect variables such as magnet current mentioned above. However, this current is not a direct measure of the exiting beam angle and position. The beam energy and the beam angle and position entering the deflection magnets also play a role. The nozzle lies at the end of a long beam train with many components, and it is typically many meters from the accelerator. Consequently, designers of scanned proton and ion beam facilities do not rely solely upon the magnet currents to monitor scanning beam position. A real-time imaging detector would thus be of great value in applications of proton beams.

Any detector is typically one of several redundant means of monitoring the system. It provides information for validating the spatially varying radiation dose that is delivered. It also provides a safety check to guard against instrument failure that could harm a patient undergoing treatment or damage the facility. Such detectors may advantageously provide real-time information that could be fed back to the control system for actively adjusting the beam to fine-tune the radiation dose.

Real-time detectors currently in use or planned for use have several deficiencies addressed by the present invention described below. An ideal detector would have a minimum of complexity, would be easily used in a hospital environment, and would introduce little material into the beam so as to minimize scattering. This detector would be fast enough and have a high enough resolution to detect the beam size and position and dose or intensity at the appropriate time scale. It should also have a reasonable lifetime and be easy to replace if necessary. Some semiconductor detectors are under development for this purpose. However, these are intrusive in that they significantly affect the proton beam and are of large complexity and thus cost. Moreover, they may not stand up to the intense radiation for very long. Ionization chambers and multi-wire detectors are currently in use for this purpose, as described by Badura et al, "Safety and Control System for the GSI Therapy Project," (ICALEPCS '97, 1997) which is incorporated herein by reference. Various aspects of their performance, however, such as their scattering, spatio-temporal resolution, and their longevity and replacement cost after radiation damage, are less than desirable.

SUMMARY OF THE INVENTION

In accordance with preferred embodiments of the present invention, an apparatus and method are provided for monitoring a spatial distribution, in a specified frame of reference, of a beam of penetrating radiation that traverses the apparatus en route to an irradiated object. The apparatus has a scintillator disposed in such a manner as to intercept the beam and an imaging detector in optical communication with the scintillator for generating a substantially instantaneous image of the beam. A processor characterizes any temporal variation of the beam on the basis, at least, of the image of the beam at more than a single instant of time.

In other embodiments of the invention, a characteristic position, such as a centroid, or a spatial distribution of charged particles in a beam, or both, may be measured. An apparatus for doing so has a scintillator disposed in such a manner as to intercept the beam, an imaging detector in optical communication with the scintillator for generating a substantially instantaneous image of the beam, and a processor for characterizing any temporal variation of at least one of the position and spatial distribution of the beam. Characterization of the position or spatial distribution of the beam is at least on the basis of the instantaneous image of the beam but may also be based upon values integrated over a specified interval of time, such as to monitor, in a clinical context, administration of a treatment fraction of radiation.

BRIEF DESCRIPTION OF THE DRAWINGS

The foregoing features of the invention will be more readily understood by reference to the following detailed description, taken with reference to the accompanying drawings, in which.

DETAILED DESCRIPTION OF SPECIFIC EMBODIMENTS

In accordance with preferred embodiments of the present invention, a beam of penetrating radiation is monitored with a scintillator. The term "penetrating radiation," as used herein, and in any appended claims, refers both to particles with mass, such as protons, as well as to photons, i.e., to electromagnetic radiation such as x-rays or gamma rays. Moreover, in the case of massive particles, the particles are typically charged, such as protons or heavier atomic ions, however, neutrons or other electrically neutral particles may also be detected, and their beams imaged in real time, within the scope of the present invention.

Figure 1:
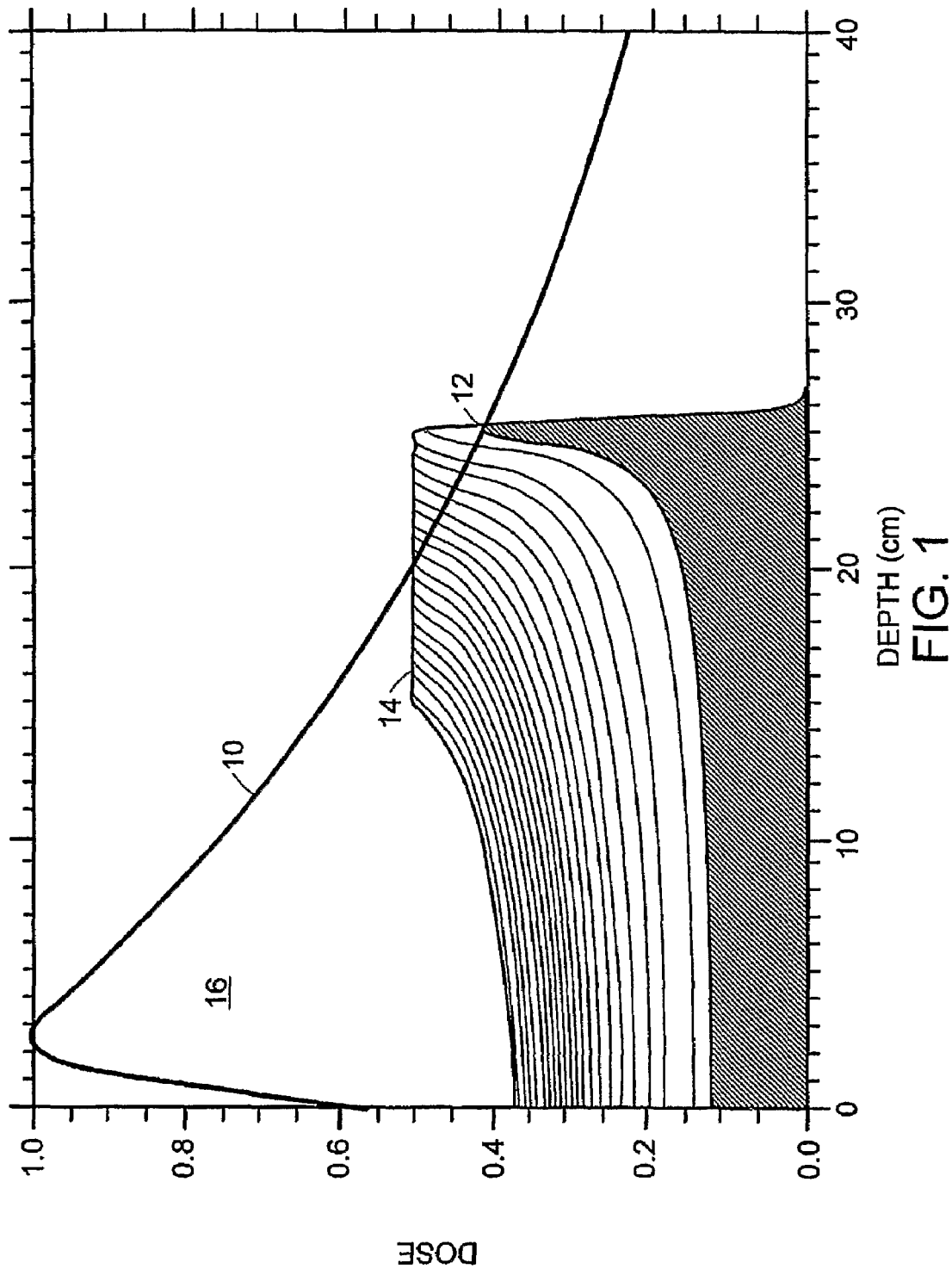
FIG. 1 depicts the relative radiation dose from a photon beam, a pristine proton beam (Bragg peak), and a spread out Bragg peak (SOBP) using protons composed of multiple pristine proton Bragg peaks of different energies. The area between the curves is the excess dose from a photon beam.
Figure 2:
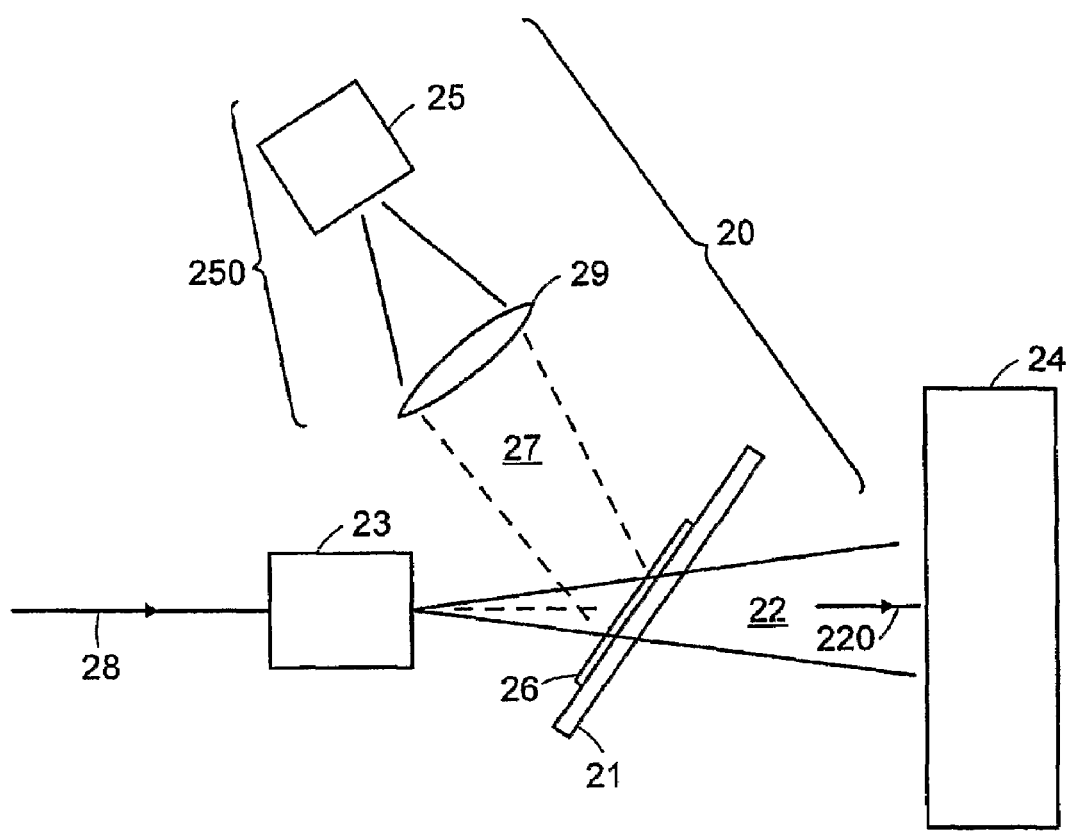
FIG. 2 shows a schematic depiction of the proton beam detector in accordance with one embodiment of the present invention.

Referring to FIG. 2, a beam monitoring apparatus is designated generally by numeral 20. A thin screen 21 is placed in a beam 22 of charged particle between a nozzle 23 (that steers charged particles 28 generated by an accelerator, not shown) and an object 24 of irradiation, typically tissue of a human subject. It is to be understood that charged particles other than protons may be employed within the scope of the present invention, but that the description will refer to protons for convenience of explication and without limitation. Similarly, while a human subject is shown as the object of irradiation, the scope of the invention is not limited thereby. Screen 21 includes a scintillator material, typically a film of inorganic scintillator 26, as discussed below. In response to the proton beam, the scintillator produces visible light 27. The light emitted by the scintillator is transferred by transfer optics 29 (signified, for illustrative purposes, and without limitation, as a single lens) and then detected by one or more sensors 25, typically including one or more imaging sensors that provide both the instantaneous beam position and integrated, spatially resolved beam profile.

In accordance with preferred embodiments of the invention, the beam monitoring apparatus 20 is sufficiently fast, both in its scintillation and imaging respects, as to be capable of tracking the beam position and dose or intensity in real time.

Using scintillator 26 as the primary detector has several advantages. First, it is relatively thin and consequently has a minimal effect on the proton beam. As shown below, scintillator 26 may be designed such that protons deposit substantially less than a per cent of their energy in the scintillator. Second, no active elements are placed in the direct proton beam. Scintillator 26 passively converts energy deposited by the proton beam 22 into light 27. The imaging sensors 25 view scintillator 26 from a distance, and can easily be shielded from any scattered radiation. Radiation damage by the proton beam is thus not a significant issue. If the beam affects the scintillator after prolonged exposure, it can easily and inexpensively be replaced. Third, this detector has excellent intrinsic spatial and temporal resolution. Scintillator screens readily achieve submillimeter resolution over large areas and some scintillators have microsecond or nanosecond response times. In addition, a typical proton therapy beam is capable of yielding greater than $10^9$ scintillation photons per second. Thus, signal levels are adequate for the beam monitor, even to track the beam with microsecond time resolution. Scintillators with microsecond, or better, time response advantageously provide for the tracking of beam position and relative intensity on that time scale.

In order to be useful for relative dosimetric purposes, i.e. determining whether the intensity modulation pattern for a specific layer of irradiation conforms to the prescription, the beam monitor must be capable of accurately measuring variations in the beam intensity. This requires that the response of detector 20 be accurately calibratable and, preferably, close to linear, though the latter is not necessary.

In order to be useful for absolute dosimetry, the response of the scintillator-imaging sensor system must be calibrated relative to known input. We discuss this issue in detail, below, but note that it is not necessary for the detector to be perfectly linear, but only for its transfer characteristics to be known.

Various types of imaging sensors may be employed to image the light 27 emitted by scintillator 26. These include active-pixel CMOS imagers, CCDs, linear and discrete photodiode arrays, and multi-anode PMTs.

In order for monitoring data to have real-time utility, not only must the scintillator and imager having microsecond time response, but the data must preferably be processed rapidly and presented to the control system with minimal delay, as discussed below.

Various considerations in the design of systems incorporating representative embodiments of the invention are now discussed.

Scintillator and Light Budget

Several considerations affect the scintillator choice. One consideration is the spectral band of the emitted light, governing the number of emitted photons per unit energy deposited. This determines whether the signal-to-noise ratio (SNR) is sufficient. Another consideration is the time response of the scintillator and its adequacy for rapid tracking of the proton beam. Other considerations include the dynamic range of the scintillator and its linearity, so that sufficiently intense radiation can be measured accurately. Finally, the effect of the scintillator on the incident radiation and its ability to withstand a high radiation dose without damage determines its scattering of the proton beam and the useful lifetime of the scintillator.

Materials that may be used as scintillator 26 include P11, P46 phosphors, and praseodymium-doped gadolinium oxysulfide (Gadox:Pr). P11 is ZnS:Ag, i.e., zinc sulfide activated with silver, a phosphor with excellent efficiency and good time response. P11 has two time components, a very rapid ~1 µs and a slower, 10-100 µs component and efficiency of ~0.1 W/W (watts light output per watt excitation with blue output peaking at 450 nm. P46 (yttrium aluminate: cerium) is faster, with decay time ~200 ns, and has green output peaking at 540 nm. P46 is less efficient than P11 but it has significant advantages in its dynamic range and radiation resistance. Gadox:Pr, with doping concentrations of order 1% have microsecond decay times and efficiencies higher than P46.

In accordance with preferred embodiments of the invention, the scintillator is deposited, using any of a variety of possible techniques, onto a substrate, such as Melinex® or Mylar®. Illustrative estimates of the proton energy deposited, respectively, in a P11 phosphor, of areal densities of 10 mg/cm² deposited on a 100 µm Melinex substrate of density 14 mg/cm² are given, in Table 1, for 80 and a 200 MeV proton passing through the screen. Thinner substrates are thus preferred, so that energy loss is not dominated by the plastic substrate.

TABLE 1

Energy deposited in P11 phosphor on Melinex scintillator

| Proton energy (MeV) | keV deposited in Melinex | keV deposited in phosphor |
|---|---|---|
| 80 | 112.9 | 60.6 |
| 200 | 58.7 | 32.2 |

Based on the phosphor efficiency and an assumed photons average wavelength of 450 nm, and representative beam currents, the photon emission per second may be estimated as presented in Table 2.

TABLE 2

Light output of the P11 phosphor per proton and for a beam

| Proton energy (MeV) | Photons/ proton | Beam current (nA) | Photons/s | Photons/100 µs |
|---|---|---|---|---|
| 80 | 2200 | 5 | 6.88E+13 | 6.88E+09 |
| 200 | 1169 | 5 | 3.65E+13 | 3.65E+09 |

Thus, ample photons are available within a 100 µs sampling window, and a strong dependence on proton energy is evident.

Regarding extension of these considerations to an x-ray beam, although the energy per particle is much less for photons than protons used in radiotherapy, the ratio of energy deposited to the energy of the particle is within a factor of order unity to that of protons. Thus, when equivalent radiation doses are considered, light output is comparable for a photon beam, allowing for mapping of dynamic photon beams within the scope of the present invention.

The light collection efficiency η is a function of the demagnification, m, of the scintillator onto the sensor, and the f/# of the lens used for imaging:

$$\eta = \frac{1}{1 + 4(f/\#)^2(m+1)^2}. \quad (1)$$

The required demagnification is a critical parameter. The field size that must be imaged is of order 30 cm square. If the detector is of order 0.5" square, the demagnification is 23.5 and the efficiency is 0.00042 with an f/1 lens. Not all photons incident are detected, however. Using a value of 20% for the quantum efficiency, the resulting number of detected photons is given in Table 3, giving a comfortably large signal.

TABLE 3

Detected photons for the beam in Table 2.

| Proton energy (MeV) | Detected Photons/s | Detected Photons/100 µs |
|---|---|---|
| 80 | 5.75E+09 | 5.75E+05 |
| 200 | 3.06E+09 | 3.06E+05 |

For beam tracking, the center of the spot can generally be found with a precision that scales as SNR$^{-1}$ times the spot width, where SNR refers to the signal-to-noise ratio. The SNR cannot exceed the limit given by photon shot noise, i.e. $\sqrt{N}$ where N is the number of detected photons. Using the 200 MeV beam parameters in Table 3, the beam center and the foregoing assumptions, the beam center may be located with 500 times the precision of the spot diameter. For the ≦10 mm scanning spots expected, this implies the spot position could be found with <0.1 mm precision. For P46, the numbers are similarly well above required levels for submillimeter accuracy. P46 has a longer output wavelength than P11 that is better matched to silicon detectors.

The achievable resolution is also affected by the scintillator spatial resolution and read noise in the sensor. These phosphor screens typically have grain sizes of several microns. Due to the grain size and thickness of the phosphor layer, scintillator spatial resolutions are typically 2-5 line pairs/mm, thus limiting the spot resolution under the foregoing assumptions.

Configuration

Figure 3:
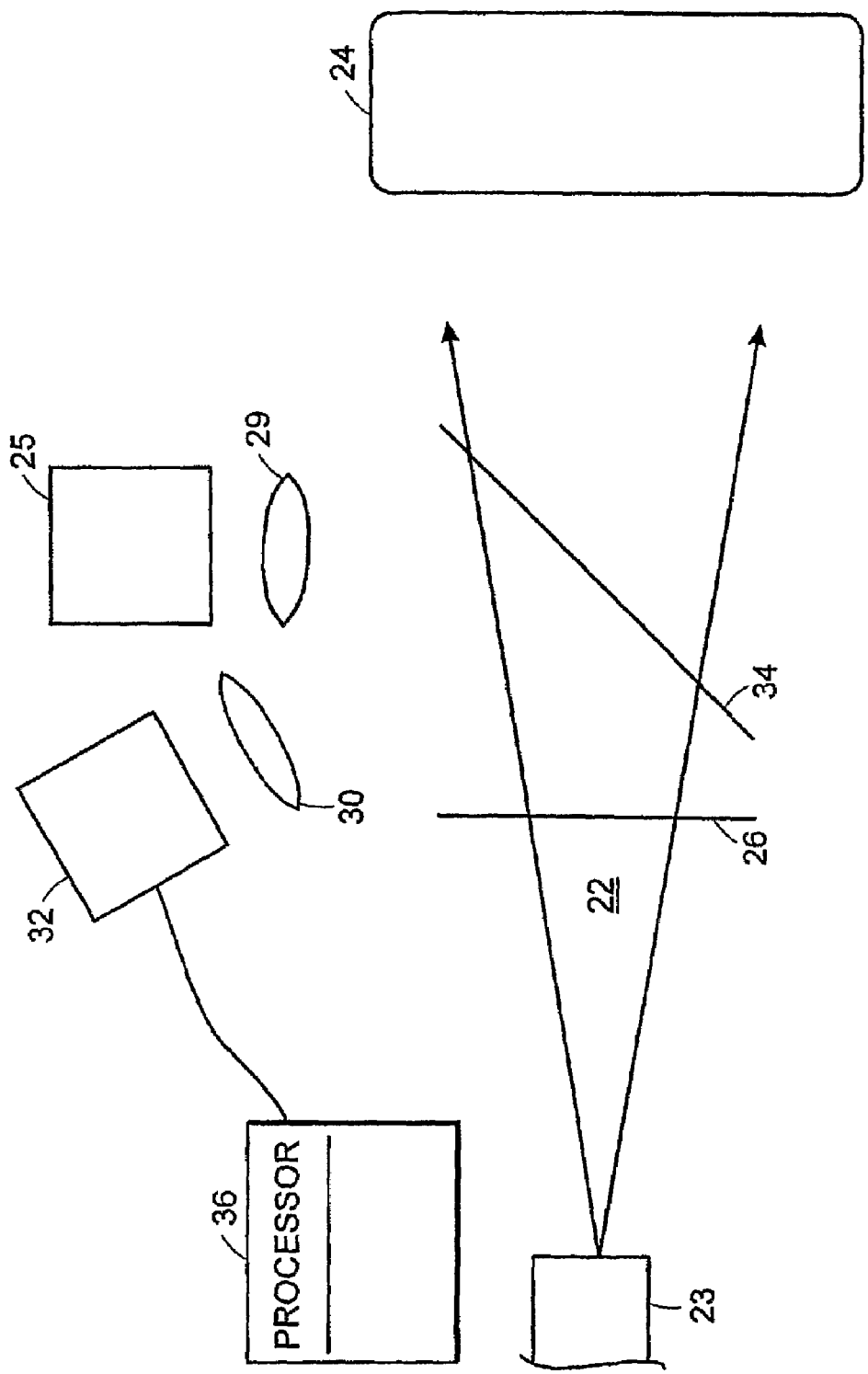
FIG. 3 shows a schematic depiction of the proton beam monitoring apparatus with two optical detectors, in accordance with another embodiment of the present invention.

In accordance with certain embodiments of the invention, a screen with P11 or P46 phosphor on Melinex serves as the scintillator. As shown in FIG. 3, the scintillator is placed normal to the beam. The scintillator is imaged onto an imaging detector. A second lens 30 and photosensor 32 may also be provided, as shown in the embodiment of FIG. 3. Second sensor 32 views the scintillator 26, as well, such as by viewing the opposite side of the scintillator from that viewed by the first sensor, or by being offset from the first sensor and views the same side, since, in some embodiments of the invention, the substrate material is clear plastic and scintillation can be observed from both sides of the scintillator. FIG. 3 also depicts the use of a fold mirror 34 for coupling light emitted by scintillator 26 into the respective fields of view of sensors 25 and 32. One sensor 25 is used to integrate the dosimetric information. The second sensor 32 tracks the proton beam in real time. In another embodiment, one sensor provides spatially resolved information while a second, such as a PMT, provides a linear measure of the scintillator output.

In accordance with preferred embodiments of the invention, a 25 mm f/0.95 lens is used to image the scintillator onto both the dosimetric sensor 25 and the beam tracking sensor 32. In accordance with a preferred embodiment of the invention, dosimetric sensor 25 is cooled CCD camera such as a camera having a 512×512 array of 20 μm pixels with 200,000 electron well depth and a 14-bit 1.3 MHz readout. The camera is preferably exposed one or more times per proton energy slice and read out in frames of ~0.2 s.

The nominal tracking sensor 32, in accordance with preferred embodiments of the invention, may be an active pixel CMOS sensor with 512×512 array of 25 μm pixels with 300,000 electron well depth and an on-chip 10-bit 8 MHz readout. Radiation tolerance is a desirable characteristic of the sensors.

In preferred embodiments of the invention, the sensor has on chip fixed pattern (offset) correction and can have a smaller region of interest read out. Thus, a small region of the sensor (a "region of interest") may advantageously be read out rapidly, within which region the proton spot should be contained. A typical region is on the order of 20×20 pixels. This provides for rapid calculation of spot position and intensity. This region of interest may be translated from readout to readout to track the spot motion.

Sensor Selection

In accordance with preferred embodiments of the invention, beam monitor 20 has two sensors. One of these is a staring imager that integrates the incident radiation painted across the patient that is evaluated for dosimetry. This detector is preferably very stable and linear, since its output is used to confirm the radiation dose. For dosimetry purposes, millimeter or sub-millimeter resolution of the dosage is desired In typical IMPT scenarios, each layer of radiation is painted across the patient several times per second within a 30 second window. A reasonable target for the feedback loop is to measure the radiation dose as every 1% is delivered, so 3.33 Hz is the nominal exposure rate for the staring sensor. Thus, each pixel records several thousand photons, on average, with an f/1 lens, per exposure. A cooled CCD is thus an advantageous choice for this sensor.

The second sensor 32 is used to track the position and size of proton beam 22 in real time. This detector preferably produces an output with ~300×400 resolution elements so as to yield millimeter resolution of the beam position. It also has much faster time response than the dosimetric sensor, of order 100 μs. This is much faster than typical array detectors of this size can read out.

Sensors that may be employed for purposes of tracking sensor 32 include, by way of example:
1. An active pixel CMOS array with rapidly variable sub-array readout;
2. Two crossed linear photodiode arrays;
3. Multi-anode photo-multiplier tube (PMT) devices with a defocused image and Anger camera centroiding; and
4. a 2-D position sensitive photoelectric device.

Active pixel CMOS imagers have ~MHz pixel readouts and region-of-interest readout that can be changed on the fly. Linear photodiode arrays can be read out very rapidly—MHz readout rates enable a 512 pixel device to be read in the 100 μs time period. While these devices can have better read noise than the active pixel CMOS devices, they require a $2^{nd}$ lens or a beamsplitter, as well as cylindrical optics to image the field onto a narrow array detector. In either case, a processor 36 digitally computes the centroid (first moment) and size (second moment or variance), employing algorithms well-known in the art.

In order to employ multi-element PMTs, which have a limited number of elements (~16, in each dimension) of elements, the beam image is spread over several elements by defocusing the image and the centroid calculated in the same fashion as an Anger camera. More exotic photoelectric devices, such as a photon counting imager or a detector with a resistive anode, may also be used within the scope of the invention.

Geometry and Packaging

Scintillator 26 is imaged onto the tracking sensor 32 using a fast lens 30. The sensors referred to, above, are typically not larger than 2.5 cm square, though they may be smaller. It is desirable to use as large a sensor as possible to minimize the required demagnification of the scintillator onto the sensor, since the optical efficiency goes inversely as the square of the demagnification.

The distance of the scintillator to the sensor also has an impact on the shielding that is required and the ease with which it can be fit into the detector, since scattered radiation decreases as the inverse square of the distance. Scattered radiation will cause bright spikes in silicon array detectors and comparable noise in photoelectric detectors. While these artifacts can be identified and removed from imagery, it is desirable to minimize them. The detector geometry and judicious use of shielding can serve to reduce the scattered radiation. A leaded glass window can be used in front of each lens and photosensor. In addition, sheets of high-Z material such as lead or tungsten, as well as borated polyethylene, can be used to shield scattered photons and neutrons, respectively, from the detector.

A first optical arrangement, shown in FIG. 2, has scintillator 26 at ~45° to a principal propagation axis 220 of the beam 22. Another arrangement, shown in FIG. 3, has the scintillator 26 substantially normal to the beam with a 45° fold mirror 34 disposed downstream with respect to the scintillator. Each geometry has advantages, and other geometries, such as with a fold mirror disposed on the nozzle-side of the scintillator, are within the scope of the invention. The first geometry has minimal material in the beam but requires more image processing. The second geometry is simpler to process but places more material in the beam. The envelope enclosing each is different, as are the susceptibilities to scattered radiation. Most proton therapy delivery nozzles will include a light field for patient alignment that is projected using a 45° fold mirror.

These nozzles may advantageously the fold mirror for both the light field and imaging the scintillator.

Regardless of the detector geometry, transformations are applied to the image data to correct for image distortion, especially when using fast lenses. The geometry with the scintillator at 45° to the beam requires more transformations. First, the rotationally symmetric proton beam will project an elliptical pattern on the scintillator. Second, the lower half of the scintillator is further from the nozzle than the upper half. This means that any divergence in the proton beam will produce a larger spot image as it moves closer to the bottom of the scintillator. But the biggest effect is that the coordinates of the image on the scintillator are not the same as the angular coordinates of the beam. A square pattern in angular coordinates maps to a trapezoid on the scintillator. In either case, the image coordinate mapping must be measured so dosimetric images can be referred to the coordinate system at the patient.

The scintillator detector 20 has two major components, scintillator screen 26 and imaging camera 250 (shown in FIG. 2), taken to include photosensor 25 and all associated transfer optics 29. The scintillator module is typically of order 30×30 $cm^2$ by 2 cm. The imaging camera is of order 10 $cm^3$. For a 25 mm focal length lens and demagnification of 24, the camera is 60 cm from the scintillator. These modules should fit easily in most scanning nozzles given that the nozzle has some length to allow magnetic deflection to paint the beam across the patient.

Dose Measurement Considerations

It is well-known that for some conditions and some scintillators, the light output is proportional neither to the input flux of radiation (particles/$cm^2$/s) nor to dE/dx, the energy deposited per particle (MeV $cm^2$/g). These non-linearities are due to a variety of effects including thermal quenching, radiation damage, electrical charge effects, and saturation of the activator sites. However, even if the scintillator output is non-linear, its response can often be predicted or calibrated so the response can be inverted to estimate the input.

Scintillators may be classified into the following four categories depending on the linearity of light output with dose over the relevant range of particle energies and flux and whether the output can be inverted:

1. Linear;
2. Linear in flux but non-linear with dE/dx, i.e., predictable;
3. Non-linear in flux but reproducible; and
4. Scintillators whose output cannot be inverted.

If the scintillator output is linear with input flux and dose per particle, i.e., type 1, it can be used for absolute dosimetry with calibration of the efficiency. A type 2 scintillator can be used for absolute dosimetry if the particle energy is known, the non-linearity with dE/dx and the efficiency are calibrated. Such scintillators are often well described by the following equation, (discussed in Birks, *The Theory and Practice of Scintillation Counting*, New York: Pergmon (1964)):

$$dL/dx = \frac{\varepsilon \, dE/dx}{1 + kB \, dE/dx} \quad (2)$$

where L is luminosity, $\varepsilon$ is the scintillator efficiency, and kB is a quenching factor for energy deposited by a single particle. The quenching factor is typically only valid over a limited range of dE/dx, and the literature has very little information on kB for inorganic scintillators. A type 3 scintillator requires additional calibration, since another term must be added to equation 1 to account for integrated dose.

It is important to note that non-linearities are highly dependent on the particular scintillator and that the transfer function can only be inverted if the output curve does not flatten out too much. It is known, however, that some scintillators can effectively be calibrated for beam parameters of interest for proton therapy, including those discussed above as useful scintillator materials.

In accordance with the invention, the scintillator is calibrated with a uniform "flat field" input, to account for any variation in the scintillator thickness or composition across the screen or any vignetting of the imaging lens. If these flat fields are carefully measured, the resulting measurements after correction can approach the limits implied by photon noise and Poisson statistics.

Data Processing

In accordance with preferred embodiments of the invention, detector 32 is an active pixel CMOS sensor that reads out at 8 MHz. Reading out a 20×20 pixel region takes ~50 μs. The data may be processed in a field programmable gate array (FPGA) using integer arithmetic. Another aspect of the processing is how the real-time tracker acquires the spot at the beginning of a scan. Ideally, the control system would present accurate information about the spot track. The tracking detector could then start its exposures with a subarray centered on the predicted spot. If the spot moves outside the subarray, a procedure to find it would involve taking an image using a larger subarray or the entire image array. For a 512×512 imager with 8 MHz readout, a full-field exposure takes 33 ms to readout. Readout of a sub-sampled array is even faster. The same centroid processing can be used and will have the same (negligible) latency, only the array is larger.

The integrating sensor also requires some image processing. Like nearly all 2D imagers, it requires two-point correction for gain and offset at each pixel. The series of short exposures must be integrated so the incident fluence is measured for each energy layer. The hardware necessary to integrate a 1-10 MHz pixel stream is inexpensive. Either a special purpose processor with <$100 of ICs or off-the-shelf hardware, available at slightly higher cost, can do these calculations with essentially zero latency. The detector can present both the individual exposures and the integrated exposure to the overall instrument control system. We point out that the control function, namely comparing these exposures to the layer intensity prescribed by the treatment plan, is the responsibility of the overall system.

Calibration

Three principal calibrations are performed for this detector: the calibration of reported proton beam position, proton beam intensity, and the 2D dosimetric integrated proton beam intensity. Both of the photosensors are pixellated devices and both bias and gain require calibration on a pixel-by-pixel basis. Additionally, 'flat-field' correction has been discussed above.

Another calibration that must be performed is the geometrical calibration. Due to distortion by the imaging lens, a Cartesian grid on a scintillator that is normal to the system axis will not map to a Cartesian grid on the imaging sensor. Calibration is therefore accomplished by illuminating the scintillator with a regular grid of spots and recording the resulting image. If the native coordinate system is Cartesian, the spots will be on a regular Cartesian grid. If the native coordinate system is angular, the spot will be on an equiangular grid emanating from the center of symmetry. Once this grid is projected and recorded, it is straightforward to solve for the offset and polynomial transformation that squares up the image. This is necessary even if the scintillator is square to the beam, due to distortion introduced by the fast lens.

Perhaps the most important calibration is the dosimetric calibration of sensor output relative to input proton beam current. As discussed above, the scintillator light output may not be a linear function of the incident radiation flux. Moreover, the output per particle will vary with particle energy.

Since protons are absorbed in the body, absorbed dose and its distribution can only be estimated non-invasively using the input radiation parameters and a 3D model of the patient. The proton pencil-beam energy, current, and spatial distribution (location and beam profile) define its dosimetric properties. The beam energy is known when the beam enters the scanning nozzle. If the detector output is calibrated appropriately for that energy, its response can be unfolded to yield the beam current as a function of time and position. The properties of the scintillator material and its uniformity, the imaging properties of the lens, and the response of the imaging detector are included in the following equation for the dose response, D, of the screen as a function of location (X,Y) on the screen, beam current I, and beam energy E $$D(x, y, E, I) = \kappa\left(\sum N_\gamma\right) = \frac{1}{\varepsilon(x, y)} \times I \times C_M(I) \times C_L(E) \times \left(\frac{1}{\rho}\frac{dE}{dx}\right). \quad (3)$$

The dose response is a function of $N_\gamma$, the (measured) number of photons collected at the CCD summed over an area representative of the pencil-beam spot. We can break down that function into terms containing the following coefficients: $\epsilon$ is the conversion and light collection efficiency as a function of the spot position, I is the beam current, $C_M$ is a current-dependent conversion factor (reflecting flux non-linearity), $C_L$ is an energy dependent factor (reflecting dE/dx nonlinearity) and $(1/\rho dE/dx)$ is the mass-stopping power as a function of the pencil-beam energy E.

We note that $\epsilon$, the flat-field response whose measurement is described above, is independent of the beam energy and current and only depends on the screen uniformity, lens, and imaging detector. This is the only parameter required for a type I scintillator. $C_L$ reflects the quenching that depends on dose per particle and is required for a type 2 scintillator. $C_M$ reflects the non-linearity with flux and is required for a type 3 scintillator.

A calibration protocol measures the above constants and functions so the scanning beam current, I(x,y,t), can be found. Such a protocol obtains each coefficient in the above equation as a relative measurement. For example, the spatial efficiency $\epsilon$ is obtained by sweeping a pencil-beam of constant current I over the surface of the screen. It is expected that $\epsilon$ is a function of geometry only. The energy and current dependent conversions, $C_M$ and $C_L$, are obtained through an explicit calibration at a single spot on the scintillation screen as the beam energy and current are varied.

By making reference to another, absolutely calibrated detector, the relative measurements can be converted to absolute measurements. Calibrations are required that quantify $\epsilon(x,y)$, $C_M$ and $C_L$, over the range of energies and beam currents of interest. Once measured, the results are numerically inverted so that measured intensities can be converted to absolute, incident flux. These calibrations must be repeated periodically with a schedule that matches the observed stability and reflect the scintillator variation with radiation dose.

Calibrations for the tracking sensor are preferably embedded in the electronics and occur in real time. The output of the dosimetric sensor is image-processed implemented in the same high level language used to correct, undistort, and store each dosimetric image.

The same optical simulator of the detector, described above, may be used to exercise the dosimetric sensor for purposes of calibration (other than those factors dependent upon scintillator radiation response). A spot is translated across the field to simulate the spot scanning.

Another software task, not strictly relating to calibration, is the removal of radiation events. The tracking and dosimetric sensors will respond to scattered radiation, both photons and neutrons that are incident. Generally, these events show up as a bright spike or streak in the image. Since the primary imagery is smooth images of a Gaussian spot with no high-contrast features, it should be easy to identify these radiation events by detecting pixels that differ from their neighbors by some number of counts that exceeds noise and smooth variation. This correction is embedded in the electronics for the tracking sensor and implemented in high-level language for the dosimetric sensor.

Optomechanical Design

In accordance with preferred embodiments of the invention, trusses are employed, made of material that matches the structure to which it will attach, to hold the scintillator and the various imaging lenses and sensors. Sheet metal enclosures that have gasketed, serpentine joints are used to make the detector light-tight, since ambient light hitting the detector may confuse or add noise or systematic drift to the measurements.

In certain applications, it is advantageous to decouple the structure that supports the shielding from the structure holding the scintillator and the lenses and sensors. The reason for this is that deformations due to lead shielding could distort the optical path, depending on how it is supported and how the structure moves. One shielding component that is typically mechanically coupled, to the sensors, is a window, typically of lead glass, disposed in front of the imaging lens, to filter photons that impact the sensors.

The described embodiments of the invention are intended to be merely exemplary and numerous variations and modifications will be apparent to those skilled in the art. All such variations and modifications are intended to be within the scope of the present invention as defined in the appended claims.

What is claimed is:

1. A radiation detector for quantitatively determining a contiguous spatial distribution of intensity of penetrating radiation characterized generally by a propagation direction between a source and an object of irradiation, the radiation detector comprising:

a spatially contiguous scintillator, disposed between the source and the object of irradiation, for emitting photons in response to the radiation; and a time-resolving sensor in optical communication with the spatially contiguous scintillator for sensing radiation intensity in real time and for providing a two-dimensional sensor output; and a dosimetric sensor for providing an integrated output indicative of a spatially-resolved cumulative radiation dose of the penetrating radiation.

2. The radiation detector as set forth in claim 1, further comprising a processor for receiving the two-dimensional sensor output and for tracking any variation with time of a spatial distribution of radiation.

3. The radiation detector as set forth in claim 1, further comprising a substrate material for supporting the scintillator in a path between the source and the object of irradiation.

4. The radiation detector as set forth in claim 3, wherein the scintillator is a film deposited upon the substrate.

5. The radiation detector as set forth in claim 1, wherein the scintillator is chosen from a group of inorganic phosphors including P11, P46, and praseodymium-doped Gadox.

6. The radiation detector as set forth in claim 4, wherein the substrate is substantially transparent to visible light.

7. The radiation detector as set forth in claim 1, further including transfer optics for optically coupling the scintillator to the time-resolving sensor.

8. The radiation detector as set forth in claim 1, further comprising a processor for receiving the two-dimensional sensor output and calculating at least one moment of the spatial distribution of the penetrating radiation beam.

9. The radiation detector as set forth in claim 2, where the tracking of any variation with time occurs in less than $1/30^{th}$ of a second.

10. The radiation detector as set forth in claim 2, where the tracking of any variation with time occurs in less than one millisecond.

11. The radiation detector as set forth in claim 2, where the tracking of any variation with time occurs in less than 200 microseconds.

12. The radiation detector as set forth in claim 1, wherein the time-resolving sensor and the dosimetric sensor are configured to view opposite sides of the scintillator.

13. The radiation detector as set forth in claim 1, wherein the time-resolving sensor and the dosimetric sensor are offset with respect to each other on a single side of the spatially contiguous scintillator.

14. A method for determining a spatial distribution and dose characterizing a beam of penetrating radiation characterized generally by a propagation direction between a source and an object of irradiation, the method comprising:
    disposing a spatially contiguous film of scintillator material between the source and the object of irradiation, for emitting photons in response to the radiation;
    sensing radiation intensity in real time by means of a time-resolving sensor in optical communication with the spatially contiguous film of scintillator material in response to traversal of the spatially contiguous film of scintillator material by penetrating radiation on a path toward the object of irradiation; and
    providing an integrated output indicative of a spatially-resolved cumulative radiation dose of the penetrating radiation by means of a dosimetric sensor.

15. A method as set forth in claim 14, further comprising generating an imaging output signal characterizing the spatial distribution of the beam.

16. A method as set forth in claim 14, further comprising calculating an instantaneous position of the beam.

17. A method as set forth in claim 14, further comprising calculating a first moment of the spatial distribution of the beam.

18. A method as set forth in claim 14, further comprising calculating a second moment of the spatial distribution of the beam.

* * * * *